United States Patent [19]  [11] 4,209,527
Sarges  [45] Jun. 24, 1980

[54] BENZIMIDAZOLONE DERIVATIVES

[75] Inventor: Reinhard Sarges, Mystic, Conn.

[73] Assignee: Pfizer Inc., New York, N.Y.

[21] Appl. No.: 39,264

[22] Filed: May 16, 1979

[51] Int. Cl.² .................. C07D 235/26; A61K 31/415
[52] U.S. Cl. ............................... 424/273 B; 548/305
[58] Field of Search ...................... 548/305; 424/273 B

[56] References Cited

U.S. PATENT DOCUMENTS

| 3,661,921 | 5/1972 | Umio | 548/305 |
| 3,821,383 | 6/1974 | Sestanj et al. | 424/258 |
| 4,161,603 | 7/1979 | Habermeier | 548/305 |

FOREIGN PATENT DOCUMENTS

| 48-28916 | 9/1973 | Japan | 548/305 |
| 48-28917 | 9/1973 | Japan | 548/305 |

OTHER PUBLICATIONS

Davoll et al., J. Chem. Soc. (London) C, 1960, pp. 314–318.

*Primary Examiner*—Natalie Trousof
*Attorney, Agent, or Firm*—Connolly and Hutz

[57] ABSTRACT

A series of novel 3-(substituted methyl)-2-oxo-1-benzimidazolinalkanoic acid compounds has been prepared, including their lower alkyl esters and unsubstituted amide derivatives, as well as the base salts of said acids with pharmacologically acceptable cations. These particular compounds are useful in therapy as aldose reductase inhibitors for the control of certain chronic diabetic complications. Typical members include those compounds derived from 2-oxo-1-benzimidazoline-acetic acid wherein a benzyl moiety is substituted at the 3-position of the molecule. Methods for preparing these compounds from known starting materials are provided.

26 Claims, No Drawings

BENZIMIDAZOLONE DERIVATIVES

BACKGROUND OF THE INVENTION

This invention relates to new and useful benzimidazolone derivatives of principal interest to those in the field of medicinal chemistry and/or chemotherapy. More particularly, it is concerned with a novel series of 3-(substituted methyl)-2-oxo-1-benzimidazolinealkanoic acid compounds, which are of especial value in view of their ability to effectively control certain chronic complications arising from diabetes mellitus (e.g., diabetic cataracts, retinopathy and neuropathy). The invention also includes a new method of therapy within its scope.

In the past, various attempts have been made by numerous investigators in the field of organic medicinal chemistry to obtain new and better oral antidiabetic agents. For the most part, these efforts have involved the synthesis and testing of various heretofore new and unavailable organic compounds, particularly in the area of the sulfonylureas, in an endeavor to determine their ability to lower blood sugar (i.e., glucose) levels to a substantially high degree when given by the oral route of administration. However, in the search for newer and still more effective antidiabetic agents, little is known about the effect of other organic compounds in preventing or arresting certain chronic complications of diabetes, such as diabetic cataracts, neuropathy and retinopathy, etc. Nevertheless, K. Sestanj et al. in U.S. Pat. No. 3,821,383 do disclose that certain aldose reductase inhibitors like 1,3-dioxo-1H-benz[d,e]-isoquinoline-2(3H)-acetic acid and some closely-related derivatives thereof are useful for these purposes even though these particular compounds are not known to be hypoglycemic per se. These particular aldose reductase inhibitors all function by inhibiting the activity of the enzyme aldose reductase, which is primarily responsible for regulating the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of various diabetic subjects are thereby prevented or otherwise reduced as the case may be. As a result, these compounds are definitely of value as aldose reductase inhibitors for controlling certain chronic diabetic complications, including those of an ocular nature, since it is already known in the art that the presence of polyols in the lens of the eye quite often leads to cataract formation together with a concomitant loss of lens clarity.

Summary of the Invention

In accordance with the present invention, it has now been rather surprisingly found that various novel 3-(substituted methyl)-2-oxo-1-benzimidazolinealkanoic acid compounds are extremely useful when employed in therapy as aldose reductase inhibitors for the control of certain chronic complications arising in a diabetic subject. More specifically, the novel compounds of this invention are all selected from the group consisting of 3-(substituted methyl)-2-oxo-1-benzimidazolinealkanoic acids of the formula:

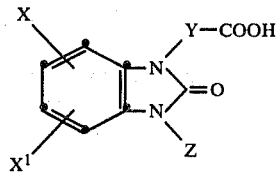

and the lower alkyl esters and unsubstituted amide derivatives thereof, and the base salts of said acids with pharmacologically acceptable cations, wherein X is hydrogen and $X^1$ is hydrogen, fluorine, chlorine, bromine, lower alkyl or lower alkoxy; or X and $X^1$, when taken separately, are each chlorine, lower alkyl or lower alkoxy, and when taken together are $-OCH_2(CH_2)_nO-$ wherein n is zero or one; Y is alkylene having from one to three carbon atoms arranged in a straight or branched chain; and Z is a member selected from the group consisting of naphthylmethyl, furfuryl, thenyl, phenylalkyl having up to three carbon atoms in the alkyl moiety and benzoylmethyl, and ring-substituted phenylalkyl having up to three carbon atoms in the alkyl moiety and ring-substituted benzoylmethyl with each ring having up to two substituents on the phenyl moiety wherein each of said ring substituents is identically chosen from the group consisting of fluorine, chlorine, bromine, trifluoromethyl, lower alkyl and lower alkoxy, or is separately chosen from the group consisting of chlorine, methyl, methoxy and trifluoromethyl. These novel compounds are all potent aldose reductase inhibitors and therefore possess the ability to markedly reduce or even inhibit sorbitol accumulation in the lens and peripheral nerves of various diabetic subjects.

Within this group of compounds are those wherein X and $X^1$ are hydrogen; Y is methylene; and Z is naphthylmethyl, phenylalkyl having up to three carbon atoms in the alkyl moiety such as benzyl, ring-substituted phenylalkyl having up to three carbon atoms in the alkyl moiety such as p-chlorobenzyl, 2,4-dichlorobenzyl, 3,4-dichlorobenzyl, p-(lower alkyl)benzyl (for example, p-methylbenzyl), p-(lower alkoxy)benzyl (for example, p-methoxybenzyl), benzoylmethyl or ring-substituted benzoylmethyl (for example, 2,4-dichlorobenzoylmethyl); or wherein X and $X^1$ are each chlorine; Y is methylene; and Z is phenylalkyl having up to three carbon atoms in the alkyl moiety such as benzyl or Z is ring-substituted phenyl alkyl having up to three carbon atoms in the alkyl moiety such as p-chlorobenzyl or 3,4-dichlorobenzyl; or wherein X and $X^1$ are hydrogen; Z is ring-substituted phenylalkyl having up to three carbon atoms in the alkyl moiety such as 3,4-dichlorobenzyl; and Y is ethylene or ethylidene.

Of especial interest in this connection are such typical and preferred member compounds of the invention such as 3-benzyl-2-oxo-1-benzimidazolineacetic acid, 3-(p-methylbenzyl)-2-oxo-1-benzimidazolineacetic acid, 3-(p-chlorobenzyl)-2-oxo-1-benzimidazolineacetic acid, 3-(p-methoxybenzyl)-2-oxo-1-benzimidazolineacetic acid, 3-(3,4-dichlorobenzyl)-2-oxo-1-benzimidazolineacetic acid, 3-(2,4-dichlorobenzyl)-2-oxo-1-benzimidazolineacetic acid, 3-(α-naphthyl)methyl-2-oxo-1-benzimidazolineacetic acid, 3-(β-naphthyl)methyl-2-oxo-1-benzimidazolineacetic acid, 3-benzyl-5,6-dichloro-2-oxo-1-benzimidazolineacetic acid, 3-(3,4-dichlorobenzyl)-5,6-dichloro-2-oxo-1-benzimidazolineacetic acid, α-[3-(3,4-dichlorobenzyl)-2- oxo-1-benzimidazoline]propionic acid and β-[3-(3,4-dichlorobenzyl)-2-oxo-1-benzimidazoline]-propionic acid, respectively. These particular compounds are all highly potent as regards their aldose reductase inhibitory activity and are therefore extremely effective for lowering sorbitol levels in the lens and sciatic nerve of diabetic subjects and galactitol levels in the lens of galactosemic subjects to a rather substantially high degree.

Detailed Description of the Invention

In accordance with the process employed for preparing the novel compounds of this invention, an appropriately substituted 2-oxo-1-benzimidazolinealkanoic acid ester of the formula:

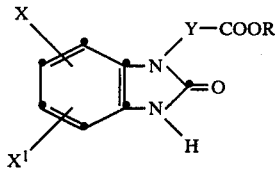

wherein X, $X^1$ and Y are all as previously defined and R is lower alkyl, is reacted with the proper organic (i.e., aralkyl or aroyl) halide of choice having the formula ZHal, where Z is as earlier defined in the structural formula for the final products and Hal is either chlorine, bromine or iodine. This particular reaction is normally carried out in the presence of a basic condensing agent such as an alkali metal hydride, alkanolate or amide, or an alkali metal-alkyl or aryl compound, as the case may be, and is usually conducted in a reaction-inert polar organic solvent, preferably using one of the N,N-di(-lower alkyl)lower alkanoamides for the present purposes at hand. Preferred solvents in this connection would definitely include N,N-dimethylformamide, N,N-diethylformamide, N,N-di(n-propyl)formamide, N,N-dimethylacetamide, N,N-diethylacetamide, N,N-dimethylpropionamide and so on. In general, substantially equimolar amounts of reactant and reagent are employed (i.e., from about 0.80 to about 1.25 mole of halide reagent with respect to the unsubstituted benzimidazolone starting material) and the reaction is effected at a temperature that is in the range from about 5° C. up to about 35° C. for a period of about 15 minutes up to about two hours. In practice, the reaction is usually conducted at room temperature for a period of time that is ordinarily less than about one hour. The basic condensing agents required for the reaction are all selected from the class of alkali metal bases previously enumerated which are sufficiently strong to form salts with the weakly acidic 3-unsubstituted-2-oxo-1-benzimidazolinealkanoic acid esters and yet mild enough not to degrade the organic molecule under the conditions of the reaction. Such basic condensing agents definitely include, for example, sodium hydride, lithium hydride and potassium hydride, etc., as well as sodium and potassium lower alkanolates like sodium methylate and potassium tert-butoxide, as well as alkali metal amides like sodamide, lithium amide, potassium amide and so on.

A variation in procedure with respect to the process of the invention involves simply starting with the appropriate 2-alkali metallo salt of the corresponding 2-oxo-1-benzimidazolinealkanoic acid ester and then treating with the desired organic halide as hereinbefore described in the absence of the basic condensing agent. However, the variation is actually one of manipulation rather than chemistry inasmuch as the alkali metal salt employed is actually first formed in situ during the course of the over-all process previously discussed. Nevertheless, the so-called alternate route may prove to be more facile and convenient at times, especially if the desired starting materials are readily at hand.

The value products produced by either of these methods, i.e., by the process of the present invention, are readily recovered from the reaction mixture (which is essentially the same in either case) by the use of any number of standard techniques well-known to those having skill in the art to which this particular type subject matter pertains. For instance, the reaction mixture may be poured into water whereby the desired benzimidazolone final product readily crystallizes out or at least precipitates from said aqueous solution. Further purification can then be achieved, if so desired, by means of recrystallization from a suitable solvent and preferably by using one of the lower alkanols such as methanol, ethanol and isopropanol, etc.

Conversion of the lower alkyl 3-(substituted methyl)-2-oxo-1-benzimidazolinealkanoic acid esters, prepared as described above, to the corresponding free acid final products of the present invention is then readily accomplished in a most convenient manner, viz., by effecting hydrolysis via the classical saponification route, preferably using dilute aqueous alkali at ambient temperatures and an alcoholic solvent medium for the reaction, followed by acidification in the usual manner with either mineral or organic acid to yield the desired 3-(substituted methyl)-2-oxo-1-benzimidazolinealkanoic acid final product. The latter product can then easily be isolated from the reaction mixture in the form of a readily-recoverable precipitate and further purified, if really deemed necessary, by means of recrystallization from a suitable solvent, preferably using a lower alkanol such as ethanol and more infrequently, an ethyl acetate/n-hexane mixture.

The unsubstituted amide derivatives of the 3-(substituted methyl)-2-oxo-1-benzimidazolinealkanoic acids of this invention are readily prepared by using standard procedures, for example, by treating the corresponding acid chloride with ammonia under basic conditions and thereafter isolating the amide final product in the usual manner. The lower alkyl esters, on the other hand, which were prepared as earlier described in the general reaction procedure of the invention (i.e., the process of this invention) can also be easily obtained in an alternate manner by merely condensing the corresponding free acid with the appropriate alcohol of choice in the presence of an acid catalyst in accordance with the conventional procedures of organic chemistry.

The starting materials required for preparing the novel 3-(substituted methyl)-2-oxo-1-benzimidazolinealkanoic acid compounds of this invention are, for the most part, known compounds or else they can easily be synthesized by those skilled in the art starting from more readily available materials according to conventional methods of organic chemistry. For instance, 2-oxo-1-benzimidazolineacetic acid ethyl ester is a known compound which has been reported by J. Davoll et. al. in the *Journal of the Chemical Society*, p. 314 (1960), while 5,6-dichloro-2-oxo-1-benzimidazolineacetic acid ethyl ester is readily obtained by using the same general procedure described in said reference starting from 4,5-dichloro-o-phenylenediamine. The higher 2-oxo-1-benzimidazolinealkanoic acid esters, on the other hand, i.e., those starting compounds where Y in the aforesaid structural formula is other than methylene, are best prepared from the corresponding known 1-isopropylene-2-oxobenzimidazole compounds by using the classical methods of organic synthesis as hereinafter described in some detail in the experimental section of this specification (e.g., see Preparations B and C, respectively).

The chemical bases which are used as reagents in this invention to prepare the aforementioned pharmaceutically acceptable base salts are those which form non-toxic salts with the herein described 3-(substituted methyl)-2-oxo-1-benzimidazolinealkanoic acid final products, such as 3-benzyl-2-oxo-1-benzimidazolineacetic acid, for example. These particular non-toxic base salts are of such a nature that their cations are said to be essentially non-toxic in character over the wide range of dosage administered. Examples of such cations include those of sodium, potassium, calcium and magnesium, etc. These salts can easily be prepared by simply treating the aforementioned 3-(substituted methyl)-2-oxo-1-benzimidazolinealkanoic acid compounds with an aqueous solution of the desired pharmacologically acceptable cation, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting solution to dryness in the same manner as before. In either case, stoichiometric quantities of reagents must be employed in order to ensure completeness of reaction and maximum production of yields with respect to the desired final product.

As previously indicated, the 3-(substituted methyl)-2-oxo-1-benzimidazolinealkanoic acid final products of this invention are all readily adapted to therapeutic use as aldose reductase inhibitors for the control of chronic diabetic complications, in view of their ability to reduce lens sorbitol levels in diabetic subjects to a statistically significant degree. For instance, 3-benzyl-2-oxo-1-benzimidazolineacetic acid, a typical and preferred agent of the present invention, is able to consistently control (i.e., inhibit) the formation of sorbitol levels in diabetic rats to a significantly high degree when given by the oral route of administration at dose levels ranging from 2.5. mg./kg. to 25 mg./kg., respectively, without showing any substantial signs of toxic side effects, The other compounds of this invention also cause similar results. Furthermore, the herein described compounds of this invention can be administered by either the oral or parenteral routes of administration, for the present purposes at hand, without causing any significant untoward pharmacological side reactions to occur in the subject to whom they are so administered. In general, these compounds are ordinarily administered in dosages ranging from about 0.25 mg. to about 25 mg. per kg. of body weight per day, although variations will necessarily occur depending upon the weight and condition of the subject being treated and the particular route of administration chosen.

In connection with the use of the 3-(substituted methyl)-2-oxo-1-benzimidazolinealkanoic acid final products of this invention for the treatment of diabetic subjects, it is to be noted that these compounds may be administered either alone or in combination with pharmaceutically acceptable carriers by either of the routes previously indicated, and that such administration can be carried out in both single and multiple dosages. More particularly, the compounds of this invention can be administered in a wide variety of different dosage forms, i.e., they may be combined with various pharmaceutically acceptable inert carriers in the form of tablets, capsules, lozenges, troches, hard candies, powders, sprays, aqueous suspensions, injectable solutions, elixirs, syryps, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for just such a purpose. In general, the therapeutically useful compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various like combinations thereof.

For purposes of parenteral administration, solutions of these particular 3-(substituted methyl)-2-oxo-1-benzimidazolinealkanoic acids in sesame or peanut oil or in aqueous propylene glycol may be employed as well as sterile aqueous solutions of the corresponding water soluble, alkali metal or alkaline-earth metal salts previously enumerated. Such aqueous solutions should be suitably buffered if necessary and the liquid diluent first rendered isotonic with sufficient saline or glucose. These particular aqueous solutions are expecially suitable for intravenous, intramuscular, subcutaneous and intraperitoneal injection purposes. In this connection, the sterile aqueous media employed are all readily obtainable by standard techniques well-known to those skilled in the art. Additionally, it is also possible to administer the aforesaid benzimidazolone compounds topically via an appropriate opthalmic solution suitable for the present purposes at hand, which can then be given dropwise to the eye.

The activity of the compounds of the present invention, as agents for the control of chronic diabetic complications, is determined by their ability to successfully pass one or more of the following standard biological and/or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats and (5) measuring their ability to delay cataract formation and reduce the severity of lens opacities in chronic galactosemic rats.

PREPARATION A 5,6-Dichloro-2-oxo-1-benzimidazolineacetic acid ethyl ester was prepared according to the procedure described by J. Davoll et al. in the *Journal of the Chemical Society*, p. 314 (1960), starting in this particular instance from 4,5-dichloro-o-phenylenediamine. The product was isolated in pure form as the ethyl ester and melted at 271°–273° C. (decomp.).

Anal. Calcd. for $C_{11}H_{10}Cl_2N_2O_3$: C,45.69; H,3.49; N,9.69. Found: C,45.68; H,3.74; N,9.66.

PREPARATION B

To a well-stirred solution consisting of 348 mg. (0.002 mole) of 1-isopropenyl-2-oxobenzimidazole [*Journal of the Chemical Society*, p. 308 (1960)] dissolved in 10 ml. of dry N,N-dimethylformamide, there was added at room temperature (~25° C.) 96 mg. (0.002 mole) of 50% sodium hydride dispersed in mineral oil. After stirring for an additional 15 minutes at room temperature, 362 mg. (0.002 mole) of ethyl 2-bromopropionate was added and the resulting mixture was thereafter stirred for a period of 30 minutes while also being maintained at this same temperature. Upon completion of this step, the spent reaction mixture was poured into water and then extracted with ethyl acetate, followed by drying of the combined organic extracts over anhydrous magnesium sulfate. After removal of the drying agent by means of filtration and the solvent by means of evaporation under reduced pressure, there was obtained an oily residue which was subsequently dissolved in ethanol and treated with 1.0 ml. of 20 N aqueous sulfuric acid. The resulting mixture was then refluxed for a period of three hours and finally evaporated to near dryness while under reduced pressure. The residue thus obtained was thereafter dissolved in ethyl acetate and successively washed with fresh separate portions of 1 N hydrochloric acid, 1 N aqueous sodium hydroxide and then finally with water. After drying the washed organic layer over anhydrous magnesium sulfate and filtering, followed by evaporation of the solvent from the filtrate while under reduced pressure, there was finally obtained 308 mg. (66%) of pure α-(2-oxo-1-benzimidazoline)propionic acid ethyl ester in the form of an oil as the residue. The pure product was subsequently characterized by means of mass spectroscopy (as well as by hydrolysis to the corresponding acid which melted at 176°–178° C.).

PREPARATION C

A solution consisting of 1.7 g. (0.01 mole) of 1-isopropenyl-2-oxobenzimidazole [*Journal of the Chemical Society*, p. 308 (1960)] dissolved in 200 ml. of dry tetrahydrofuran was prepared at room temperature and treated with 1.0 g. (0.01 mole) of ethyl acrylate in the presence of 1.0 ml. of Triton B (the registered trademark name of the Aldrich Chemical Company, Inc. of Milwaukee, Wisconsin for their brand of benzyl trimethyl ammonium hydroxide). The resulting mixture was then refluxed for a period of two hours and finally evaporated to near dryness while under reduced pressure to afford a residue. The latter material was subsequently dissolved in ethyl acetate and washed well with water, followed by drying over anhydrous magnesium sulfate. After removal of the drying agent by means of filtration and the solvent by means of evaporation under reduced pressure, there was obtained a fresh residue which was subsequently dissolved in 100 ml. of ethanol and treated with 5 ml. of 20 N aqueous sulfuric acid. The latter acidic mixture was then allowed to stand at room temperature (~25° C.) for a period of 40 hours. Upon completion of this step, the spent reaction mixture was evaporated to near dryness while reduced pressure and the resulting residue thereafter dissolved in ethyl acetate. After washing the latter solution in a successive manner with fresh separate portions of water and dilute aqueous sodium bicarbonate, respectively, followed by drying over anhydrous magnesium sulfate in the usual manner, there was finally obtained a clear dry filtrate which was then concentrated in vacuo to afford the desired product as residue. Recrystallization of the latter from diethyl ether/n-hexane then gave 1.58 g. (68%) of pure β-(2-oxo-1-benzimidazoline)propionic acid ethyl ester, m.p. 93°–97° C. The pure product was subsequently characterized by means of mass spectroscopy.

EXAMPLE 1

To a well-stirred solution consisting of 880 mg. (0.004 mole) of 2-oxo-1-benzimidazolineacetic acid ethyl ester [prepared according to the procedure described by J. Davoll et al. in the *Journal of the Chemical Society*, p.314 (1960)] dissolved in 20 ml. of dry N,N-dimethylformamide, there was added at room temperature (~25° C.) 184 mg. (0.004 mole) of 50% sodium hydride dispersed in mineral oil. After stirring for an additional 15 minutes at room temperature, 684 mg. (0.004 mole) of benzyl bromide was added and the resulting mixture was thereafter stirred for a period of 30 minutes while also being maintained at this same temperature. Upon completion of this step, the spent reaction mixture was slowly poured into 300 ml. of water and the precipitated solids were subsequently collected by means of suction-filtration, washed well with water and then air dried to constant weight. Recrystallization of the crude material from ethanol then gave 535 mg. (43%) of pure 3-benzyl-2-oxo-1-benzimidazolineacetic acid ethyl ester, m.p. 122°–124° C.

Anal. Calcd. for $C_{18}H_{18}N_2O_3$: C,69.66; H,5.84; N,9.03. Found: C,70.03; H,5.90; N,9.26.

EXAMPLE 2

The procedure described in Example 1 was repeated (using the molar proportions as before) except that 440 mg. (0.002 mole) of 2-oxo-1-benzimidazolineacetic acid ethyl ester and 370 mg. (0.002 mole) of α-bromo-p-xylene were reacted to afford 510 mg. (79%) of pure 3-(p-methylbenzyl)-2-oxo-1-benzimidazolineacetic acid ethyl ester, m.p. 103°–105° C.

Anal. Calcd. for $C_{19}H_{20}N_2O_3$: C,70.35; H,6.22; N,8.64. Found: C,70.20; H,6.27; N,8.54.

EXAMPLE 3

The procedure described in Example 1 was repeated (using the same molar proportions as before) except that 880 mg. (0.004 mole) of 2-oxo-1-benzimidazolineacetic acid ethyl ester and 640 mg. (0.004 mole) of p-chlorobenzyl chloride were reacted to afford 1.03 g. (75%) of pure 3-(p-chlorobenzyl)-2-oxo-1-benzimidazolineacetic acid ethyl ester, m.p. 134°–137° C.

Anal. Calcd. for $C_{16}H_{13}Cl_2N_2O_3$: C,60.57; H,4.14; N,8.85. Found: C,60.55; H,4.35; N,8.86.

EXAMPLE 4

The procedure described in Example 1 was repeated (using the same molar proportions as before) except that 440 mg. (0.002 mole) of 2-oxo-1-benzimidazolineacetic acid ethyl ester and 313 mg. (0.002 mole) of p-methoxybenzyl chloride were reacted to afford 510 mg. (75%) of pure 3-(p-methoxybenzyl)-2-oxo-1-benzimidazolineacetic acid ethyl ester, m.p. 123°–125° C.

Anal. Calcd. for $C_{19}H_{20}N_2O_4$: C,67.04; H,5.92; N,8.23. Found: C,67.29; H,6.14; N,8.15.

EXAMPLE 5

The procedure described in Example 1 was repeated (using the same molar proportions as before) except that 2.2 g. (0.01 mole) of 2-oxo-1-benzimidazolineacetic acid ethyl ester and 1.95 g. (0.01 mole) of 3,4-dichlorobenzyl chloride were reacted to afford 1.72 g. (45%) of pure 3-(3,4-dichlorobenzyl)-2-oxo-1-benzimidazolineacetic acid ethyl ester, m.p. 124°–126° C.

Anal. Calcd. for $C_{18}H_{16}Cl_2N_2O_3$: C,57.00; H,4.25; N,7.39. Found: C,56.67; H,4.17; N,7.46.

EXAMPLE 6

The procedure described in Example 1 was repeated (using the same molar proportions as before) except that 440 mg. (0.002 mole) of 2-oxo-1-benzimidazolineacetic acid ethyl ester and 319 mg. (0.002 mole) of 2,4-dichlorobenzyl bromide were reacted to afford 382 mg. (50%) of pure 3-(2,4-dichlorobenzyl)-2-oxo-1-benzimidazolineacetic acid ethyl ester, m.p. 124°–126° C.

Anal. Calcd. for $C_{18}H_{16}Cl_2N_2O_3$: C,57.00; H,4.25; N,7.39. Found: C,56.46; H,4.11; N,7.19.

EXAMPLE 7

The procedure described in Example 1 was repeated (using the same molar proportions as before) except that 440 mg. (0.002 mole) of 2-oxo-1-benzimidazolineacetic acid ethyl ester and 353 mg. (0.002 mole) of 1-chloromethylnaphthalene were reacted to afford 340 mg. (47%) of 3-($\alpha$-naphthyl)methyl-2-oxo-1-benzimidazolineacetic acid ethyl ester, m.p. 113°–116° C. The analytical sample melted at 116°–118° C. after recrystallization from diethyl ester/n-hexane and was further characterized by means of mass spectroscopy.

EXAMPLE 8

The procedure described in Example 1 was repeated (using the same molar proportions as before) except that 440 mg. (0.002 mole) of 2-oxo-1-benzimidazolineacetic acid ethyl ester and 353 mg. (0.002 mole) of 2-chloromethylnaphthalene were reacted to afford 583 mg. (81%) of 3-($\beta$-naphthyl)methyl-2-oxo-1-benzimidazolineacetic acid ethyl ester, isolated as an oil.

EXAMPLE 9

The procedure described in Example 1 was repeated (using the same molar proportions as before) except that 440 mg. (0.002 mole) of 2-oxo-1-benzimidazolineacetic acid ethyl ester and 447 mg. (0.002 mole) of 2,2',4'-trichloroacetophenone were reacted to afford 380 mg. of crude product. Purification of the latter material was then achieved by means of column chromatography over silica gel, using ethyl acetate/n-hexane (2:1 by volume) as the eluant, to afford 146 mg. (18%) of pure 3-(2,4-dichlorobenzoylmethyl)-2-oxo-1-benzimidazolineacetic acid ethyl ester as a tan solid. The product was subsequently characterized by means of mass spectroscopy.

EXAMPLE 10

The procedure described in Example 1 was repeated (using the same molar proportions as before) except that 210 mg. (0.0007 mole) of 5,6-dichloro-2-oxo-1-benzimidazolineacetic acid ethyl ester (prepared according to the procedure described in Preparation A) and 120 mg. (0.0007 mole) of benzyl bromide were reacted to afford crude 3-benzyl-5,6-dichloro-2-oxo-1-benzimidazolineacetic acid ethyl ester, which was used as such in the next reaction step (viz., hydrolysis to the corresponding acid as hereinafter described in Example 24) without any further purification being necessary.

EXAMPLE 11

The procedure described in Example 1 was repeated (using the same molar proportions as before) except that 240 mg. (0.0008 mole) of 5,6-dichloro-2-oxo-1-benzimidazolineacetic acid ethyl ester and 134 mg. (0.00083 mole) of p-chlorobenzyl chloride were reacted to afford 3-(p-chlorobenzyl)-5,6-dichloro-2-oxo-1-benzimidazolineacetic acid ethyl ester as the desired final product.

EXAMPLE 12

The procedure described in Example 1 was repeated (using the same molar proportions as before) except that 289 mg. (0.001 mole) of 5,6-dichloro-2-oxo-1-benzimidazolineacetic acid ethyl ester and 195 mg. (0.001 mole) of 3,4-dichlorobenzyl chloride were reacted to afford 309 mg. (69%) of 3-(3,4-dichlorobenzyl)-5,6-dichloro-2-oxo-1-benzimidazolineacetic acid ethyl ester, m.p. 149°–152° C. after recrystallization from n-hexane. The analytical sample melted at 152°–154° C. after a further recrystallization from ethyl acetate/n-hexane.

Anal. Calcd. for $C_{18}H_{14}Cl_4N_2O_3$: C,48.24; H,3.15; N,6.25. Found: C,48.29; H,3.30; N,6.33.

EXAMPLE 13

The procedure described in Example 1 was repeated (using the same molar proportions as before) except that 300 mg. (0.0013 mole) of $\alpha$-(2-oxo-1-benzimidazoline)-propionic acid ethyl ester (prepared according to the procedure described in Preparation B) and 254 mg. (0.0013 mole) of 3,4-dichlorobenzyl chloride were reacted to afford $\alpha$-[3-(3,4-dichlorobenzyl)-2-oxo-1-benzimidazoline]-propionic acid ethyl ester as the desired final product.

EXAMPLE 14

The procedure described in Example 1 was repeated (using the same molar proportions as before) except that 702 mg. (0.003 mole) of $\beta$-(2-oxo-1-benzimidazoline)-propionic acid ethyl ester (prepared according to the procedure described in Preparation C) and 585 mg. (0.003 mole) of 3,4-dichlorobenzyl chloride were reacted to afford $\beta$-[3-(3,4-dichlorobenzyl)-2-oxo-1-benzimidazoline]propionic acid ethyl ester as the desired final product.

EXAMPLE 15

A solution consisting of 425 mg. (0.0014 mole) of 3-benzyl-2-oxo-1-benzimidazolineacetic acid ethyl ester (prepared as described in Example 1) dissolved in 10 ml. of ethanol was treated with 1.4 ml. of 1 N aqueous sodium hydroxide and 2 ml. of water. After stirring for 30 minutes at room temperature (~25° C.), the basified aqueous reaction mixture was diluted with 5 ml. of water and then acidified with 3 N aqueous hydrochloric acid. The precipitated solids so obtained were then collected by means of suction filtration, washed well with water and air dried to constant weight to give 345 mg. (88%) of pure 3-benzyl-2-oxo-1-benzimidazolineacetic acid, m.p. 200°–203° C. The melting point of the analytical sample was 200°–202° C. after recrystallization from ethanol.

Anal. Calcd for $C_{16}H_{14}N_2O_3$: C,68.07; H,5.00; N,9.93. Found: C,68.20; H,5.13; N, 9.96.

EXAMPLE 16

The procedure described in Example 15 was repeated except for the fact that 440 mg. (0.00136 mole) of pure 3-(p-methylbenzyl)-2-oxo-1-benzimidazolineacetic acid ethyl ester (prepared as described in Example 2) was used as the substrate in the hydrolysis reaction (in place of 3-benzyl-2-oxo-1-benzimidazolineacetic acid ethyl ester), using the same molar proportions as before. In this particular case, the corresponding final product obtained was 3-(p-xylyl)-2-oxo-1-benzimidazolineacetic acid, m.p. 196°–198° C. The yield of pure product amounted to 370 mg. (92%).

Anal. Calcd. for $C_{17}H_{16}N_2O_3$: C,68.90; H,5.44; N,9.46. Found: C,68.50; H,5.28; N,9.39.

EXAMPLE 17

The procedure described in Example 15 was repeated except for the fact that 680 mg. (0.00215 mole) of pure 3-(p-chlorobenzyl)-2-oxo-1-benzimidazolineacetic acid ethyl ester (prepared as described in Example 3) was used as the substrate in the hydrolysis reaction (in place of 3-benzyl-2-oxo-1-benzimidazolineacetic acid ethyl ester), using the same molar proportions as before). In this particular case, the corresponding final product obtained was 3-(p-chlorobenzyl)-2-oxo-1-benzimidazolineacetic acid, m.p. 201°–203° C. The yield of pure product amounted to 415 mg. (66%).

Anal. Calcd. for $C_{16}H_{13}Cl_4N_2O_3$: C,60.67; H,4.14; N,8.85. Found: C,60.55; H,4.35; N,8.86.

EXAMPLE 18

The procedure described in Example 15 was repeated except for the fact that 340 mg. (0.001 mole) of pure 3-(p-methoxybenzyl)-2-oxo-1-benzimidazolineacetic acid ethyl ester (prepared as described in Example 4) was used as the substrate in the hydrolysis reaction (in place of 3-benzyl-2-oxo-1-benzimidazolineacetic acid ethyl ester), using the same molar proportions as before. In this particular case, the corresponding final product obtained was 3-(p-methoxybenzyl)-2-oxo-1-benzimidazolineacetic acid, m.p. 200°–202° C. The yield of pure product amounted to 112 mg. (36%).

Anal. Calcd. for $C_{17}H_{16}N_2O_4.0.25H_2O$: C,64.44; H,5.26; N, 8.84. Found: C,64.16; H,4.99; N,8.72.

EXAMPLE 19

The procedure described in Example 15 was repeated except for the fact that 379 mg. (0.001 mole) of pure 3-(3,4-dichlorobenzyl)-2-oxo-1-benzimidazolineacetic ethyl ester (prepared as described in Example 5) was used as the substrate in the hydrolysis reaction (in place of 3-benzyl-2-oxo-1-benzimidazolineacetic acid ethyl ester), using the same molar proportions as before. In this particular case, the corresponding final product obtained was 3-(3,4-dichlorobenzyl)-2-oxo-1-benzimidazolineacetic acid, m.p. 183°–185° C. The yield of pure product amounted to 255 mg. (73%).

Anal. Calcd. for $C_{16}H_{12}Cl_2N_2O_3$: C,55.15; H,3.70; N,7.57. Found: C,54.88; H,3.63; N,7.59.

EXAMPLE 20

The procedure described in Example 15 was repeated except for the fact that 350 mg. (0.00092 mole) of pure 3-(2,4-dichlorobenzyl)-2-oxo-1-benzimidazolineacetic acid ethyl ester (prepared as described in Example 6) was used as the substrate in the hydrolysis reaction (in place of 3-benzyl-2-oxo-1-benzimidazoleacetic acid ethyl ester), using the same molar proportions as before. In this particular case, the corresponding final product obtained was 3-(2,4-dichlorobenzyl)-2-oxo-1-benzimidazolelineacetic acid, m.p. 210°–212° C. The yield of pure product amounted to 203 mg. (63%).

Anal. Calcd. for $C_{16}H_{12}Cl_2N_2O_3$: C,54.72; H,3.45; N,7.98. Found: C,55.05; H,3.89; N,7.74.

EXAMPLE 21

The procedure described in Example 15 was repeated except for the fact that 300 mg. (0.00083 mole) of 3-(α-naphthyl)methyl-2-oxo-1-benzimidazolineacetic acid ethyl ester (prepared according to the procedure described in Example 7) was used as the substrate in the hydrolysis reaction (in place of 3-benzyl-2-oxo-1-benzimidazolineacetic acid ethyl ester), using the same molar proportions as before. In this particular case, the corresponding final product obtained was 3-(α-naphthyl)methyl-2-oxo-1-benzimidazolineacetic acid, m.p. 208°–210° C. The yield of pure product amounted to 145 mg. (53%).

Anal. Calcd. for $C_{20}H_{16}N_2O_3$: C,72.28; H,4.85; N,8.43. Found: C,72.10; H,5.00; N,8.30.

EXAMPLE 22

The procedure described in Example 15 was repeated except for the fact that 583 mg. (0.00162 mole) of 3-(β-naphthylmethyl)-2-oxo-1-benzimidazolineacetic acid ethyl ester (prepared according to the procedure described in Example 8) was used as the substrate in the hydrolysis reaction (in place of 3-benzyl-2-oxo-1-benzimidazolineacetic acid ethyl ester), using the same molar proportions as before. In this particular case, the corresponding final product obtained was 3-(β-naphthyl)methyl-2-oxo-1-benzimidazolineacetic acid, m.p. 209°–211° C. The yield of pure product amounted to 124 mg. (23%).

Anal. Calcd. for $C_{20}H_{16}N_2O_3$: C,72.28; H,4.85. N,8.43. Found: C,71.96; H,4.95; N,8.34.

EXAMPLE 23

The procedure described in Example 15 was repeated except for the fact that 146 mg. (0.00036 mole) of pure 3-(2,4-dichlorobenzoylmethyl)-2-oxo-1-benzimidazolineacetic acid ethyl ester (prepared according to the procedure described in Example 9) was used as the substrate in the hydrolysis reaction (in place of 3-benzyl-2-oxo-1-benzimidazolineacetic acid ethyl ester), using the same molar proportions as before. In this particular case, the corresponding final product obtained was 3-(2,4-dichlorobenzoylmethyl)-2-oxo-1-benzimidazolineacetic acid, m.p. 230°–230° C. (decomp). The yield of pure product amount to 29 mg. (21%).

Anal. Calcd. for $C_{17}H_{12}Cl_2N_2O_4.0.5H_2O$: C,52.59; H,3.37; N,7.29. Found: C,52.81; H,3.39; N,7.22.

EXAMPLE 24

The procedure described in Example 15 was repeated except for the fact that the entire yield of crude 3-benzyl-5,6-dichloro-2-oxo-1-benzimidazolineacetic acid ethyl ester obtained according to the procedure described in Example 10 was used as the substrate in the hydrolysis reaction (in place of 3-benzyl-2-oxo-1-benzimidazolineacetic acid ethyl ester), using the same molar proportions as before. In this particular case, the corresponding final product obtained was 3-benzyl-5,6-dichloro-2-oxo-1-benzimidazolineacetic acid, m.p. 211°–213° C. The yield of pure product amounted to 135 mg. (55%).

Anal. Calcd. for $C_{16}H_{12}Cl_2N_2O_3.0.5C_2H_5OH$: C,54.55; H,4.04; N,7.48. Found: C,54.03; H,3.98; N,7.63.

EXAMPLE 25

The procedure described in Example 15 was repeated except for the fact that the entire yield of the isolated 3-(p-chlorobenzyl)-5,6-dichloro-2-oxo-1-benzimidazolineacetic acid ethyl ester product obtained according to the procedure described in Example 11 was used as the substrate in the hydrolysis reaction (in place of 3-benzyl-2-oxo-1-benzimidazolineacetic acid ethyl ester), using the same molar proportions as before. In this particular case, the corresponding final product obtained was 3-(p-chlorobenzyl)-5,6-dichloro-2-oxo-1-benzimidazolineacetic acid, m.p. 213°–216° C. (decomp). The yield of pure product amounted to 63 mg. (20%) and the latter material was subsequently characterized by means of mass spectroscopy.

EXAMPLE 26

The procedure described in Example 15 was repeated except for the fact that 250 mg. (0.00067 mole) of 3-(3,4-dichlorobenzyl)-5,6-dichloro-2-oxo-1-benzimidazolineacetic acid ethyl ester (prepared according to the procedure described in Example 12) was used as the substrate in the hydrolysis reaction (in place of 3-benzyl-2-oxo-1-benzimidazolineacetic acid ethyl ester), using the same molar proportions as before. In this particular case, the corresponding final product obtained was 3-(3,4-dichlorobenzyl)-5,6-dichloro-2-oxo-1-benzimidazolineacetic acid, m.p. 212°–214° C. after recrystallization from ethyl acetate/n-hexane. The yield of pure product amounted to 170 mg. (72%).

Anal. Calcd. for $C_{18}H_{14}Cl_4N_2O_3$: C,45.74; H,2.40; N,6.67. Found: C,45.56; H,2.62; N,6.71.

EXAMPLE 27

The procedure described in Example 15 was repeated except for the fact that the entire yield of the isolated α-[3-(3,4-dichlorobenzyl)-2-oxo-1-benzimidazoline]-propionic acid ethyl ester product obtained according to the procedure described in Example 13 was used as the substrate in the hydrolysis reaction (in place of 3-benzyl-2-oxo-1-benzimidazolineacetic acid ethyl ester), using the same molar proportions as before. In this particular case, the corresponding final product obtained was α-[3-(3,4-dichlorobenzyl)-2-oxo-1-benzimidazoline]propionic acid, m.p. 176°–178° C. The yield of pure product amounted to 23 mg. (5%).

Anal. Calcd. for $C_{17}H_{14}Cl_2N_2O_3$: C,55.90; H,3.86; N,7.67. Found: C,55.88; H,3.93; N,7.68.

EXAMPLE 28

The procedure described in Example 15 was repeated except for the fact that the entire yield of the isolated β-[3-(3,4-dichlorobenzyl)-2-oxo-1-benzimidazoline]propionic acid ethyl ester product obtained according to the procedure described in Example 14 was used as the substrate in the hydrolysis reaction (in place of 3-benzyl-2-oxo-1-benzimidazolineacetic acid ethyl ester), using the same molar proportions as before. In this particular case, the corresponding final product obtained was β-[3-(3,4-dichlorobenzyl)-2-oxo-1-benzimidazoline]propionic acid, m.p. 169°–171° C. The yield of pure product amounted to 366 mg. (34%).

Anal. Calcd. for $C_{17}H_{14}Cl_2N_2O_3$: C,55.90; H,3.86; N,7.67. Found: C,56.04; H,4.01; N,7.68.

EXAMPLE 29

The following 3-(substituted methyl)-2-oxo-1-benzimidazolinealkanoic acid final products are prepared by employing the procedures described in the previous examples, starting from readily available materials in each instance:

3-benzyl-5- and 6-fluoro-2-oxo-1-benzimidazolineacetic acid 3-benzyl-5- and 6-chloro-2-oxo-1-benzimidazolineacetic acid 3-benzyl-5- and 6-bromo-2-oxo-1-benzimidazolineacetic acid 3-benzyl-5- and 6-methyl-2-oxo-1-benzimidazolineacetic acid 3-benzyl-5- and 6-(n-butyl)-2-oxo-1-benzimidazolineacetic acid 3-benzyl-5- and 6-methoxy-2-oxo-1-benzimidazolineacetic acid 3-benzyl-5- and 6-isobutoxy-2-oxo-1-benzimidazolineacetic acid 3-benzyl-5,6-dimethyl-2-oxo-1-benzimidazolineacetic acid 3-benzyl-5,6-di(n-butyl)-2-oxo-1-benzimidazolineacetic acid 3-benzyl-5,6-dimethoxy-2-oxo-1-benzimidazolineacetic acid 3-benzyl-5,6-di(n-butoxy)-2-oxo-1-benzimidazolineacetic acid 3-benzyl-5,6-methylenedioxy-2-oxo-1-benzimidazolineacetic acid 3-benzyl-5,6-ethylenedioxy-2-oxo-1-benzimidazolineacetic acid 3-(β-naphthyl)methyl-5- and 6-chloro-2-oxo-1-benzimidazolineacetic acid 3-(α-naphthyl)methyl-5- and 6-ethoxy-2-oxo-1-benzimidazoline acetic acid 3-(α-furfuryl-2-oxo-1-benzimidazolineacetic acid 3-(β-furfuryl)-5- and 6-chloro-2-oxo-1-benzimidazolineacetic acid 3-(2-thenyl)-2-oxo-1-benzimidazolineacetic acid 3-(3-thenyl)-5- and 6-chloro-2-oxo-1-benzimidazolineacetic acid 3-(β-phenylethyl)-2-oxo-1-benzimidazolineacetic acid 3-(γ-phenylpropyl)-5- and 6-chloro-2-oxo-1-benzimidazolineacetic acid 3-benzoylmethyl-2-oxo-1-benzimidazolineacetic acid 3-benzoylmethyl-5,6-dichloro-2-oxo-1-benzimidazolineacetic acid 3-(o-fluorobenzyl-2-oxo-1-benzimidazolineacetic acid 3-(m-chloro-γ-phenylpropyl)-2-oxo-1-benzimidazolineacetic acid 3-(p-bromobenzyl)-2-oxo-1-benzimidazolineacetic acid
3-(m-trifluoromethyl-β-phenylethyl)-2-oxo-1-benzimidazolineacetic acid
3-(m-isopropylbenzyl)-2-oxo-1-benzimidazolineacetic acid
3-p-ethoxy-β-phenylethyl)-2-oxo-1-benzimidazolineacetic acid
3-(2,4-dimethylbenzyl)-2-oxo-1-benzimidazolineacetic acid
3-(2,5-dimethoxybenzoylmethyl)-2-oxo-1-benzimidazolineacetic acid
3-(5-chloro-2-methoxybenzoylmethyl)-2-oxo-1-benzimidazolineacetic acid
3-(2-methoxy-5-methylbenzoylmethyl)-2-oxo-1-benzimidazolineacetic acid
3-(p-chlorobenzoylmethyl)-2-oxo-1-benzimidazolineacetic acid
3-(p-methoxybenzoylmethyl)-2-oxo-1-benzimidazolineacetic acid
α-(3-benzyl-2-oxo-1-benzimidazoline)propionic acid
β-[3-(2-thenyl)-2-oxo-1-benzimidazoline]propionic acid
β-[3-(α-furfuryl)-2-oxo-1-benzimidazoline]acetic acid
β-[3-(α-naphthyl)methyl-2-oxo-1-benzimidazoline]propionic acid
α-[3-(β-phenylethyl)-2-oxo-1-benzimidazoline]propionic acid
β-[3-(γ-phenylpropyl)-2-oxo-1-benzimidazoline]propionic acid
α-[3-(p-methylbenzyl)-2-oxo-1-benzimidazoline]propionic acid
β-[3-(p-chlorobenzyl)-2-oxo-1-benzimidazoline]propionic acid
α-[3-(p-methoxybenzyl)-2-oxo-1-benzimidazoline]propionic acid
β-[3-(2,4-dimethylbenzyl)-2-oxo-1-benzimidazoline]propionic acid

EXAMPLE 30

A solution consisting of 3.1 g. (0.01 mole) of pure 3-benzyl-2-oxo-1-benzimidazolineacetic acid (prepared according to the procedure described in Example 15) dissolved in 100 ml. of ethanol is saturated with dry hydrogen chloride gas, and the resultant mixture is then refluxed for a period of approximately four hours. Upon completion of this step, the solvent is removed by means of evaporation under reduced pressure and the residue subsequently made alkaline by the addition thereto of a saturated aqueous sodium bicarbonate solution. The resulting solution is then extracted with diethyl ether, and the combined ethereal extracts are subsequently dried over anhydrous sodium sulfate and filtered. After removal of the drying agent by means of filtration and the solvent in the usual manner, there is obtained crude ester product in the form of a solid crystalline residue. Recrystallization of the latter material from ethanol then affords the pure ethyl ester of 3-benzyl-2-oxo-1-benzimidazolineacetic acid, identical in every respect with the product earlier obtained in Example 1.

EXAMPLE 31

The procedure described in Example 30 is repeated except for the fact that methanol is the reagent employed instead of ethanol and the methyl ester of 3-benzyl-2-oxo-1-benzimidazolineacetic acid is the corresponding final product thus obtained.

In like manner, the n-propyl, isopropyl, n-butyl, isobutyl, n-amyl, isoamyl and n-hexyl esters of 3-benzyl-2-oxo-1-benzimidazolineacetic acid are also similarly prepared by merely employing the appropriate alcohol of choice in place of ethanol in each particular case.

EXAMPLE 32

The procedure described in Example 30 is repeated except that β-[3-(3,4-dichlorobenzyl)-2-oxo-1-benzimidazoline]propionic acid (prepared according to the procedure described in Example 28) is the starting material employed in place of 3-benzyl-2-oxo-1-benzimidazolineacetic acid for the present purposes at hand. In this particular case, the corresponding final product thus obtained is the ethyl ester of β-[3-(3,4-dichlorobenzyl)-2-oxo-1-benzimidazoline]propionic acid.

In like manner, the methyl, n-propyl, isopropyl, n-butyl, isobutyl, n-amyl, isoamyl and n-hexyl esters of 3-benzyl-2-oxo-1-benzimidazolineacetic acid are also each similarly prepared, as are the corresponding lower alkyl esters of the other 3-(substituted methyl)-2-oxo-1-benzimidazolinealkanoic acids of this invention which are reported in Examples 16–27 and 29, respectively.

EXAMPLE 33

A mixture of 1.55 g. (0.005 mole) of 3-benzyl-2-oxo-1-benzimidazolineacetic acid and 10 ml. of thionyl chloride dissolved in 300 ml. of chloroform is refluxed for a period of approximately 2.5–4 hours. After cooling to room temperature (~25° C.), the reaction mixture is slowly poured into a solution consisting of 4.5 g. of sodium hydroxide dissolved in 100 ml. of ammonium hydroxide. The resulting chloroform layer is then separated and subsequently evaporated to near dryness while under reduced pressure to give a residual solid. Recrystallization of the latter material from ethanol-water then yields pure 3-benzyl-2-oxo-1-benzimidazolineacetamide in fine crystalline form.

EXAMPLE 34

The procedure described in Example 33 is repeated except that β-[3-(3,4-dichlorobenzyl)-2-oxo-1-benzimidazoline]propionic acid is the starting material employed in place of 3-benzyl-2-oxo-1-benzimidazolineacetic acid for the present purposes at hand. In this particular case, the corresponding final product thus obtained is β-[3-(3,4-dichlorobenzyl)-2-oxo-1-benzimidazoline]propionamide.

In like manner, the unsubstituted amides of the other 3-(substituted methyl)-2-oxo-1-benzimidazolinealkanoic acids of this invention are also similarly prepared by merely employing the appropriate acid starting material of choice (taken from Examples 16–27 and 29, respectively) in each particular case.

EXAMPLE 35

The sodium salt of 3-benzyl-2-oxo-1-benzimidazolineacetic acid is prepared by dissolving said compound in water containing an equivalent amount in moles of sodium hydroxide and then freeze-drying the mixture. In this way, the desired alkali metal salt of the acid is obtained in the form of an amorphous powder which is freely-soluble in water.

In like manner, the potassium and lithium salts are also similarly prepared, as are the other alkali metal salts of all the other 3-(substituted methyl)-2-oxo-1-benzimidazolinealkanoic acids of this invention which are reported earlier in Examples 16–29, respectively.

EXAMPLE 36

The calcium salt of 3-benzyl-2-oxo-1-benzimidazolineacetic acid is prepared by dissolving said compound in water containing an equivalent amount in moles of calcium hydroxide and then freeze-drying the mixture. The corresponding magnesium salt is also prepared in like manner, as are all the other alkaline-earth metal salts not only of this particular compound, but also of those acids previously described in Examples 16–29, respectively.

EXAMPLE 37

A dry solid pharmaceutical composition is prepared by blending the following materials together in the proportions by weight specified below:

| | |
|---|---|
| 3-Benzyl-2-oxo-1-benzimidazoline-acetic acid | 50 |
| Sodium citrate | 25 |
| Alginic acid | 10 |
| Polyvinylpyrrolidone | 10 |
| Magnesium stearate | 5 |

After the dried compound is thoroughly blended, tablets are punched from the resulting mixture, each tablet being of such size that it contains 200 mg. of the active ingredient. Other tablets are also prepared in a similar fashion containing 25, 50 and 100 mg. of the action ingredient, respectively, by merely using the appropriate amount of the benzimidazolone compound in each case.

EXAMPLE 38

A dry solid pharmaceutical composition is prepared by combining the following materials together in the proportions by weight indicated below:

| | |
|---|---|
| β-[3-(3,4-Dichlorobenzyl)-2-oxo-1-benzimidazoline]propionic acid | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE 39

The following 3-(substituted methyl)-2-oxo-1-benzimidazolinealkanoic acid final products of Examples 15–24 and 26–28, respectively, were tested at a concentration level of $10^{-4}M$ for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In every case, the substrate employed was partially purified aldose reductase enzyme obtained from calf lens. The results obtained with each compound are expressed below in terms of their percent inhibition of enzyme activity (%) with respect to the particular concentration level chosen ($10^{-4}M$):

| Compound | % Inhibition at $10^{-4}M$ |
|---|---|
| Product of Example 15 | 84 |
| Product of Example 16 | 86 |
| Product of Example 17 | 88 |
| Product of Example 18 | 88 |
| Product of Example 19 | 89 |
| Product of Example 20 | 87 |
| Product of Example 21 | 92 |
| Product of Example 22 | 86 |
| Product of Example 23 | 71 |
| Product of Example 24 | 89 |
| Product of Example 26 | 82 |
| Product of Example 27 | 91 |
| Product of Example 28 | 90 |

I claim:

1. A compound selected from the group consisting of 3-(substituted methyl)-2-oxo-1-benzimidazoline-alkanoic acids of the formula:

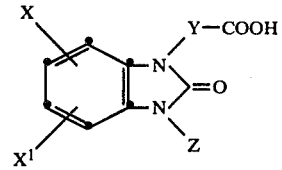

and the lower alkyl esters and unsubstituted amide derivatives thereof, and the base salts of said acids with pharmacologically acceptable cations wherein X is hydrogen and $X^1$ is hydrogen, fluorine, chlorine, bromine, lower alkyl or lower alkoxy; or X and $X^1$, when taken separately, are each chlorine, lower alkyl or lower alkoxy, and when taken together are —$OCH_2(CH_2)_nO$— wherein n is zero or one;

Y is alkylene having from one to three carbon atoms arranged in a straight or branched chain; and Z is a member selected from the group consisting of naphthylmethyl, furfuryl, thenyl, phenylalkyl having up to three carbon atoms in the alkyl moiety and benzoylmethyl, and ring-substituted phenylalkyl having up to three carbon atoms in the alkyl moiety and ring-substituted benzoylmethyl with each ring having up to two substituents on the phenyl moiety wherein each of said ring substituents is identically chosen from the group consisting of fluorine, chlorine, bromine, trifluoromethyl, lower alkyl and lower alkoxy, or is separately chosen from the group consisting of chlorine, methyl, methoxy and trifluoromethyl.

2. A compound as claimed in claim 1 wherein X and $X^1$ are each hydrogen, Y is methylene and Z is naphthylmethyl.

3. A compound as claimed in claim 1 wherein X and $X^1$ are each hydrogen, Y is methylene and Z is phenylalkyl having up to three carbon atoms in the alkyl moiety.

4. A compound as claimed in claim 3 wherein Z is benzyl.

5. A compound as claimed in claim 1 wherein X and $X^1$ are each hydrogen, Y is methylene and Z is ring-substituted phenylalkyl having up to three carbon atoms in the alkyl moiety.

6. A compound as claimed in claim 5 wherein Z is p-chlorobenzyl.

7. A compound as claimed in claim 5 wherein Z is 2,4-dichlorobenzyl.

8. A compound as claimed in claim 5 wherein Z is 3,4-dichlorobenzyl.

9. A compound as claimed in claim 5 wherein Z is p-(lower alkyl)benzyl.

10. A compound as claimed in claim 9 wherein Z is p-methylbenzyl.

11. A compound as claimed in claim 5 wherein Z is p-(lower alkoxy)benzyl.

12. A compound as claimed in claim 11 wherein Z is p-methoxybenzyl.

13. A compound as claimed in claim 1 wherein X and $X^1$ are each hydrogen, Y is methylene and Z is benzoylmethyl.

14. A compound as claimed in claim 1 wherein X and $X^1$ are each hydrogen, Y is methylene and Z is ring-substituted benzoylmethyl.

15. A compound as claimed in claim 14 wherein Z is 2,4-dichlorobenzoylmethyl.

16. A compound as claimed in claim 1 wherein X and $X^1$ when taken separately, are each chlorine, Y is methylene and Z is phenylalkyl having up to three carbon atoms in the alkyl moiety.

17. A compound as claimed in claim 16 wherein Z is benzyl.

18. a compound as claimed in claim 1 wherein X and $X^1$, when taken separately, are each chlorine, Y is methylene and Z is ring-substituted phenylalkyl having up to three carbon atoms in the alkyl moiety.

19. A compound as claimed in claim 18 wherein Z is p-chlorobenzyl.

20. A compound as claimed in claim 18 wherein Z is 3,4-dichlorobenzyl.

21. A compound as claimed in claim 1 wherein X and $X^1$ are each hydrogen, Y is ethylene and Z is ring-substituted phenylalkyl having up to three carbon atoms in the alkyl moiety.

22. A compound as claimed in claim 21 wherein Z is 3,4-dichlorobenzyl.

23. A compound as claimed in claim 1 wherein X and $X^1$ are each hydrogen, Y is ethylidene and Z is ring-substituted phenylalkyl having up to three carbon atoms in the alkyl moiety.

24. A compound as claimed in claim 23 wherein Z is 3,4-dichlorobenzyl.

25. A method for treating a diabetic host to prevent or alleviate diabetes-associated chronic complications arising in said host, which comprises administering to said diabetic host an effective amount of a compound as claimed in claim 1.

26. A composition suitable for oral administration comprising a pharmaceutically acceptable carrier and a compound as claimed in claim 1 in an amount effective for the treatment of diabetes-associated chronic complications.

* * * * *